United States Patent [19]

Shue

[11] Patent Number: 4,940,023

[45] Date of Patent: Jul. 10, 1990

[54] HIGH RESOLUTION STETHOSCOPIC APPARATUS

[76] Inventor: Ming-Jeng Shue, No. 14, Lane 8, Chung-I Street, Taichung City, Taiwan

[21] Appl. No.: 272,312

[22] Filed: Nov. 17, 1988

[51] Int. Cl.⁵ .............................................. A61B 7/02
[52] U.S. Cl. ..................................... 128/715; 128/773
[58] Field of Search .................. 128/715, 773; 381/67, 381/151, 159, 169, 182

[56] References Cited

U.S. PATENT DOCUMENTS

| | | | |
|---|---|---|---|
| 3,130,275 | 4/1964 | Hagey | 381/67 X |
| 3,160,708 | 12/1964 | Andries et al. | 128/715 X |
| 3,275,099 | 9/1966 | Speelman | 128/715 X |
| 3,999,625 | 12/1976 | Pickett et al. | 128/715 X |
| 4,362,164 | 12/1982 | Little et al. | 128/715 X |
| 4,784,154 | 11/1988 | Shirley et al. | 128/773 X |

FOREIGN PATENT DOCUMENTS 2115934 9/1983 United Kingdom ............... 128/715

Primary Examiner—Angela D. Sykes
Attorney, Agent, or Firm—Pasquale A. Razzano

[57] ABSTRACT

A stethoscopic apparatus with a plurality of improved chestpieces is disclosed. Each chestpiece in the stethoscopic apparatus of the invention includes a base member and a resonance membrane connected to the base member. The resonance membrane has a plateau-shaped protrusion formed thereon which forms a sealed resonance chamber between the base member and the resonance membrane. The resonance membrane is preferably made of plastic polymers and the periphery of the resonance membrane is thermal set to form a relatively stiff rim for engaging with the base member of the chest member. Since the resonance membrane provides a compulsory resonance chamber during the operation of the stethoscopic apparatus, the resolution ability of the chestpiece is greatly improved.

12 Claims, 7 Drawing Sheets

HIGH RESOLUTION STETHOSCOPIC APPARATUS

BACKGROUND OF THE INVENTION

1. Field of the Invention

The present invention relates to a stethoscopic apparatus, and more particularly to a stethoscope equipped with a plurality of chestpieces to be chosen for use by a doctor which are capable of highly resoluting the heart sounds detected.

2. Brief Description of the Prior Art

Conventional stethoscopes are indispensable medical instruments enabling doctors to diagnose the diseases of their patients. A typical conventional stethoscope is shown in FIG. 1 generally consisting of an open bell or Ford chestpiece 1, a closed diaphragm or Bowles chestpiece 2, a tubing 3 for the transmission of the heart sounds detected by the chestpieces, and a pair of headsets 4 and eartips 5. Several disadvantages related especially to the chestpieces were found in the conventional stethoscopes.

When a doctor uses a conventional stethoscope, he has to push the Ford chestpiece 1 against the body of the patient so that an airtight sealed resonance chamber may be formed for the purpose of detecting low pitch body sounds such as third and fourth heart sounds, mitral and tricuspid murmurs, etc.. However, a conventional Ford chestpiece does not enable the easy formation of the afore said resonance chamber especially when the patient is dressed or wrapped in bandages. Therefore, the sounds detected by the conventional Ford chestpiece are usually incomplete, thus affecting seriously the accuracy of the diagnosis.

A conventional Bowles chestpiece 2 is usually equipped with a diaphragm for the detection of those body sounds of higher frequencies such as first and second heart sounds, the ejection sounds and clicks, the opening snap of mitral or tricuspid stenosis, the murmurs of aortic or pulmonary valve regurgitation, the murmurs of interventricular septal defects, etc.. It has been noted that when the Bowles chestpiece is placed against the body of a patient, significant tension will be applied to the soft tissue beneath the diaphragm of the chestpiece. Therefore, the higher frequency portion of the vibration wave of those visceras is easily conducted to the body surface. This is the reason why moderate pressure must be exerted onto the body surface while using the Bowles chestpiece.

For better contact feeling with a patient's body, the conventional Ford chestpiece 1 is equipped with an O-ring 1a made of a soft material. It is easily understood that the O-ring will effect the body contact situation.

The conventional Bowles chestpiece includes a fixation rim 2b for the diaphragm 2a which is made of either metal, rubber or plastic. There is usually a height difference between the diaphragm 2a and the fixation rim 2b. Therefore it is relatively difficult to make ideal contact between the chestpiece and the body's surface for receiving the vibration waves from the viscera via said body's surface and diaphragm. Moreover, on account of the existence of the conventional indispensible fixation rim, the free vibration of the diaphragm in accordance with the vibration wave of the viscera and the body's surface will be highly limited by the fixation rim. Therefore, there is a definite defect in the transformation of the visceral vibration waves into sound waves transmitted via the body's surface, the diaphragm, and the vibration air chamber under the diaphragm. Besides, given the fact that male threads and female threads must be provided on the chestpiece and the rim respectively for the installation of the diaphragm, the overall structure of the chestpieces is complicated.

A conventional stethoscope includes only two chestpieces. Doctors have no further choice except to use the handy Ford and Bowles chestpieces on the stethoscope. This limits the scope of use of conventional stethoscopes.

A multi-functional radio/wire stethoscopic apparatus was disclosed in U.S. Pat. No. 4,723,555 issued to the same inventor as of this application. This patent is mentioned and incorporated here for the purpose of better understanding the present invention and also for the reference of those portions of the structure identical to the same in the present invention.

SUMMARY OF THE INVENTION

It is therefore the principle object of the present invention to provide a stethoscopic apparatus having a plurality of improved chestpieces for obviating the disadvantages of the conventional stethoscopes.

Another object of the present invention is to provide a stethoscopic apparatus having chestpieces thereof fixed in a very simple structure without the equipment of the fixation rim.

The chestpieces of the stethoscopic apparatus of the present invention are characterized by their high resolution ability.

The structure of chestpiece of the stethoscopic apparatus of the present invention comprises a base with a plateau shaped resonance membrane mounted thereon for achieving a better body contact situation as well as a better resolution of the body sounds being detected.

The resonance membrane of the chestpieces in the stethoscopic apparatus of the present invention is made of plastic polymers having a thermal set rim for connecting to the base of the chestpiece. The height and diameter of the plateau of the resonance membrane can be varied to accommodate patients of different ages. The stethoscopic apparatus of the present invention is designed to include a plurality of chestpieces of different dimensions to accommodate the resonance membranes thereof. The user, usually a doctor, may then have the option to choose different types and combinations of the chestpieces on the stethoscopic apparatus.

An important feature of the stethoscopic apparatus is that the height of the plateau of the resonance membrane is preferably one to two times the diameter of the sound communication opening formed in the center of the base of the chestpieces, resulting in an improved resolution ability.

Accordingly, the stethoscopic apparatus according to the present invention comprises a handle member for the installation of operation devices such as a sound amplifying means, a radio transmitting means and a plurality of chestpieces connected to a housing member for the detection of the body sounds of a patient, each of said chestpieces being characterized by a plateau-shaped base, and a resonance membrane made of plastic polymers mounted on said base, to achieve a higher resolution ability for the stethoscope in detecting body sounds. Each of said chestpieces is further characterized in that the resonance membrane with the plateau of each said chestpieces is of a preset diameter to achieve better contact with the body of a patient.

BRIEF DESCRIPTION OF THE DRAWINGS

Those and other objects, features and advantages of the stethoscopic apparatus according to the present invention will become apparent from the following detailed description of the preferred embodiments with reference to the accompanying drawings, in which.

DETAILED DESCRIPTION OF THE PREFERRED EMBODIMENTS

Figure 1:
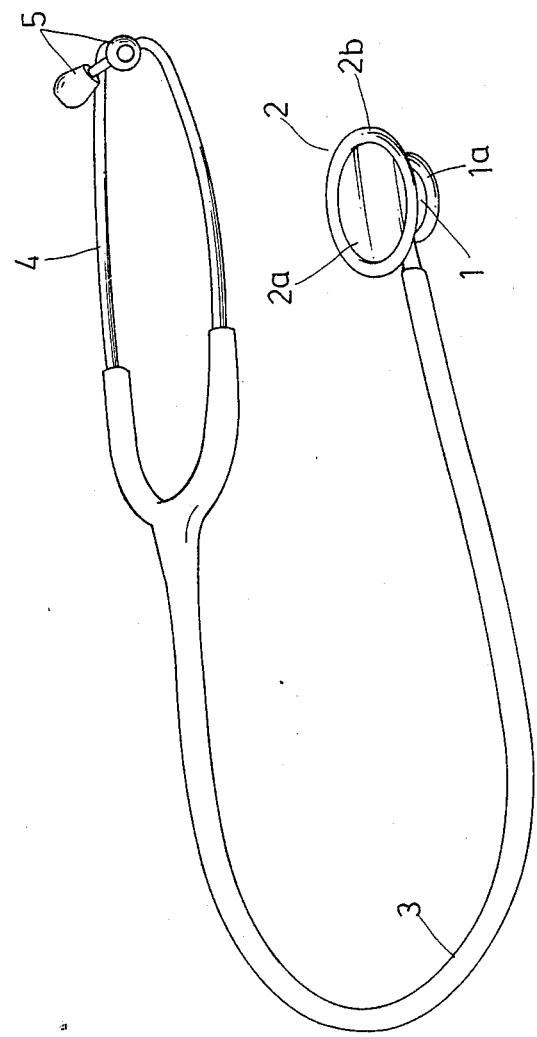
FIG. 1 is a perspective view of a conventional stethoscope.
Figure 2:
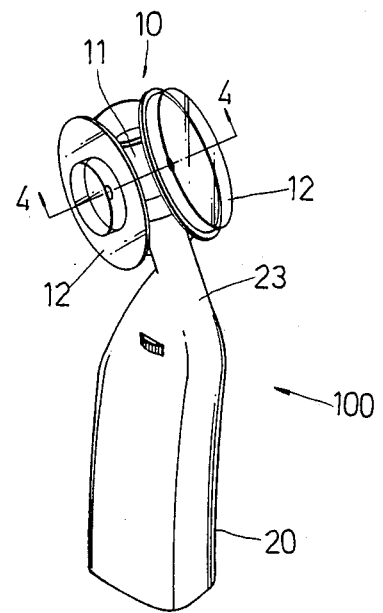
FIG. 2 is a perspective view of a preferred embodiment of the stethoscopic apparatus according to the present invention.
Figure 3:
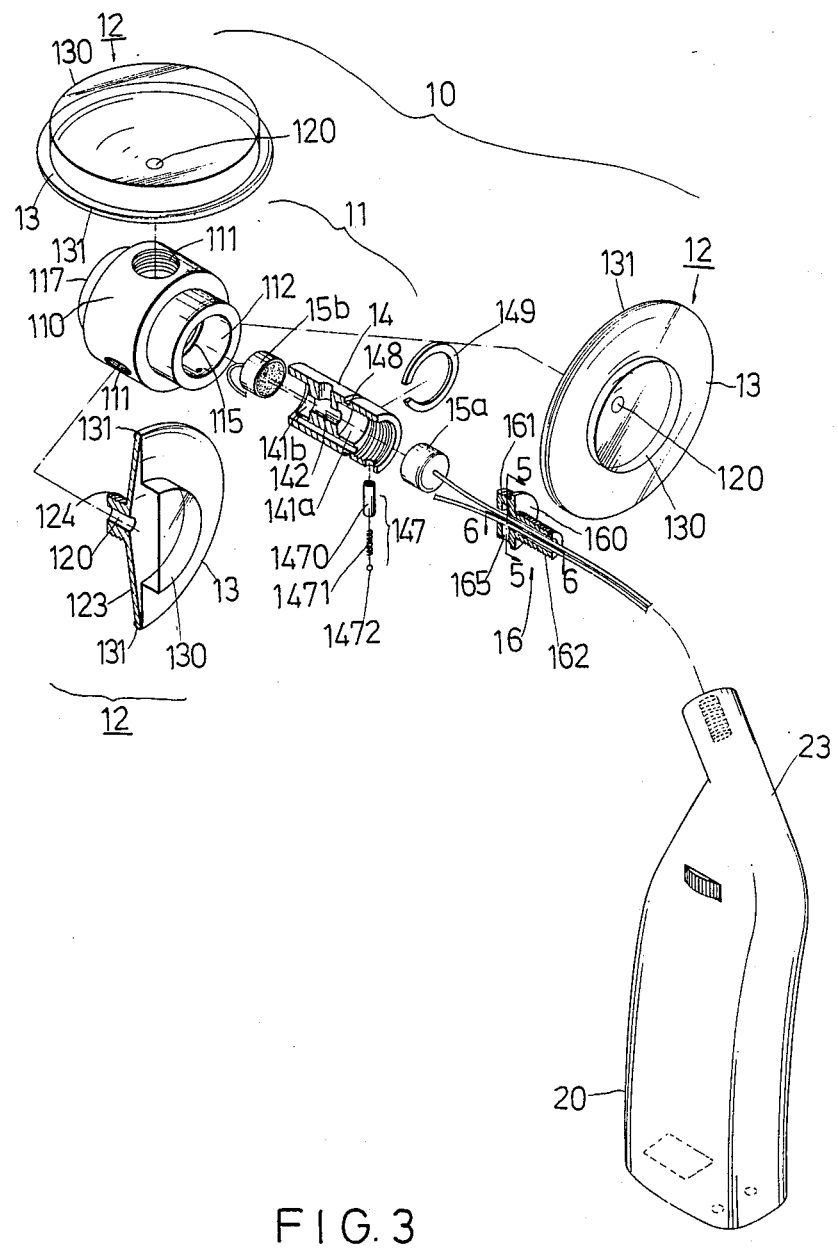
FIG. 3 is an enlarged exploded view of the stethoscopic apparatus shown in FIG. 2.

Referring to FIGS. 2 and 3 which show the perspective and exploded views of the stethoscopic apparatus of the present invention, the apparatus 100 generally comprises a handle member 20 with a neck portion 23 formed and extended from an upper portion of the handle member 20, a chestpiece assembly 10 which further includes a body member 11 and a plurality of chestpieces 12, and an adaptor 16 which serves as a connector and is disposed between said body member 11 and said handle member 20. The handle member 20 is generally of a rectangular container shape for the installation of all the operation devices such as an amplifier, a radio transmission circuit device, and batteries, etc.. The detailed structure of the handle member 20 has already been disclosed in the patent specification of U.S. Pat. No. 4,723,555, which shall be incorporated here as part of the disclosure of the present invention.

Figure 4:
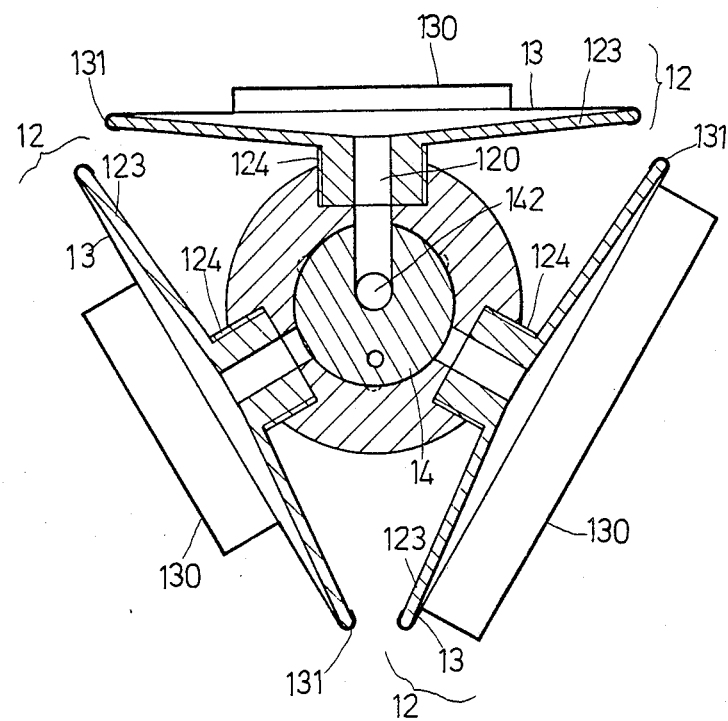
FIG. 4 is an enlarged sectional view taken along line 4—4 of the chestpieces in the stethoscopic apparatus in FIG. 2.

Referring particularly to FIG. 3, the body member 11 of the chestpiece assembly 10 further includes a housing member 110 with one end thereof formed as a sealed end 117 and a cylindrical chamber 112 formed therein, a rotatable shaft 14 within the chamber 112 and a pair of microphones 15a, 15b respectively installed in the accommodation spaces 141a, 141b formed within said rotatable shaft 14. An annular recess 115 is formed on the inner surface of said cylindrical chamber 112 to match with another annular recess 148 formed on the outer surface of said rotatable shaft 14. A clip 149 is positioned in said recesses 115 and 148 for preventing the relative axial movement between the rotatable shaft 14 and the housing member 110. There are three receiving openings 111 symmetrically distributed around said housing member 110. Each receiving opening 111 has a female thread formed therein. Three chestpieces 12 are also included in the assembly 10. Each chestpiece 12 comprises a substantially concave disc-shaped base member 123 with a stem 124 formed and extended from a central part thereof, and a resonance membrane 13 having an engaging rim 131 conforming to said base member 123 and a plateau-shaped protrusion 130. The resonance membrane 13, best shown in FIG. 4, is made of plastic polymers and is thermal-set at the peripheral area thereof forming an engaging rim 131 enabling engagement with said base member 123 of the chestpiece 12. The stem 124 of the base member 123 has a male thread formed on the outer surface thereof for fitting with the female thread of the receiving opening 111. The resonance membrane 13 of the chestpiece 12 is very important to the function and utility of the stethoscopic apparatus and shall be described in greater detail hereinbelow.

Referring to FIG. 3 with reference to FIG. 4, the housing member 110 of the body member 11 has three receiving openings 111 for the connection of three chestpieces 12. It is easily understood that each chestpiece 12 has male threads formed on the stem 124 thereof for engaging with the female threads formed on the inner surface of said receiving opening 111. Doctors can choose different chestpieces and connect these to the housing member 110 to suit different needs.

Figure 5:
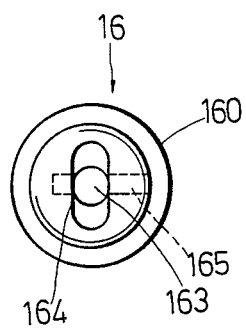
FIG. 5 is an enlarged sectional view taken along line 5—5 of the adaptor for the chestpieces in the stethoscopic apparatus in FIG. 3.
Figure 6:
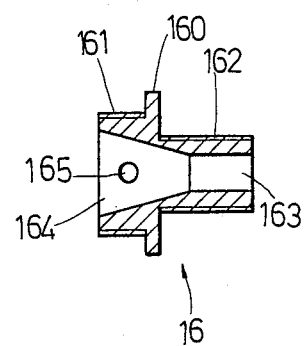
FIG. 6 is another enlarged sectional view taken along line 6—6 of the adaptor for the chestpieces in the stethoscopic apparatus in FIG. 3.

The adaptor 16 of the chestpiece assembly 10 is best shown in FIGS. 5 and 6 where sectional views best illustrate the structure of the adaptor 16 and the interconnective relationship with the rotatable shaft 14. The adaptor 16 comprises a rear threaded end 162 to enable connection with the handle member 20 by means of a bore 163 formed therein, a forward threaded end 161, slightly larger in its diameter than that of the rear end 162, with a horn-shaped interior space 164 formed therein and a bore 165 extending in a direction perpendicular to the axis of the adaptor 16 but not extending through said adaptor's forward end 161, and a flange 160 annularly extending from the outer surface of the adaptor 16 between said two ends 161, 162. In assembly, a combination 147 of a pin 1470, a bias spring 1471 and a ball 1472 is inserted into said bore 165. The adaptor 16 is then connected to said rotatable shaft 14. There are male threads formed on the outer surface of the end 162 of the adaptor 16 for the connection of the same with said neck portion 23 of the handle member 20. The function of the ball 1472 is for the user, usually a doctor, to determine by touch that a proper match has been achieved between the sound communication opening 120 of chestpiece 12 and the sound passage 142 in the rotatable shaft 14, as shown in FIG. 4.

Figure 7:
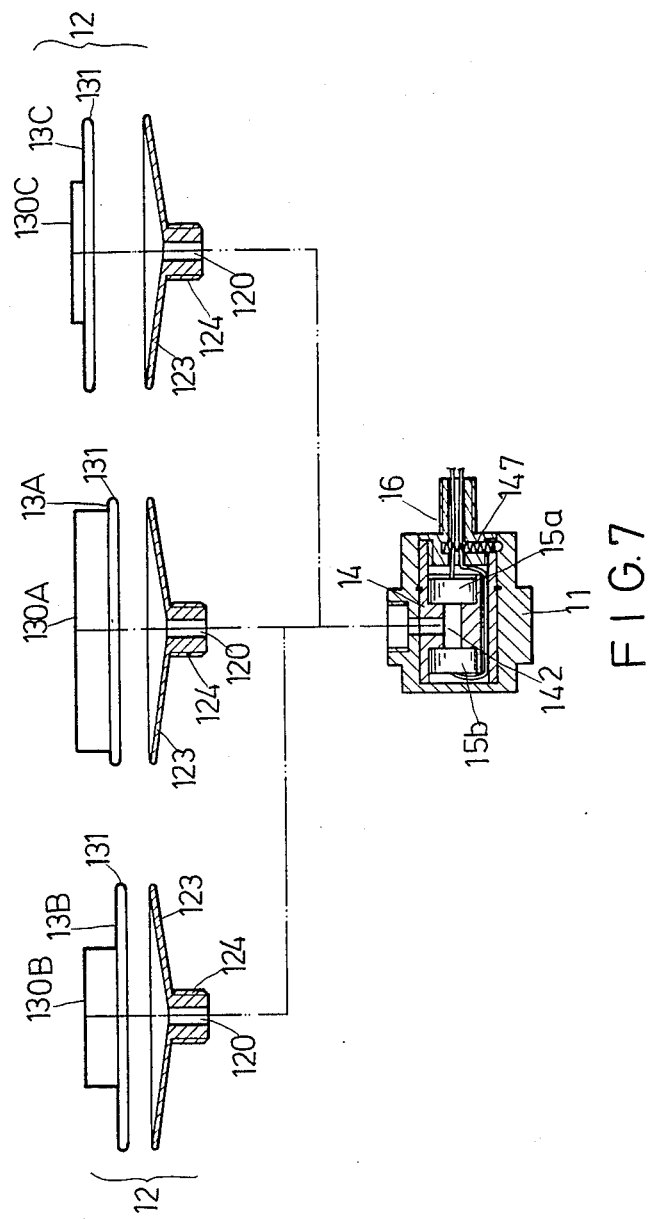
FIG. 7 is a schematic sectional view of the chestpieces in the stethoscopic apparatus of the present invention.

Referring to FIG. 7, which shows schematic sectional views of the chestpieces in the stethoscopic apparatus of the present invention, it is found that the shape and the dimension of each chestpiece may be varied for the purpose of diagnosing patients of different ages and body sizes. Since each chestpiece 12 is equipped with a resonance membrane 13 having a plateau-shaped protrusion 130, effective body-surface contact is achieved without the need for exerting pressure on said body surface. In FIG. 7, all the chestpieces 12 with various resonance membranes 13A, 13B, 13C are suitable for detecting body sounds of higher frequencies. In another words, the chestpieces 12 are used as Bowles chestpieces. According to the invention, the diameters of the plateau-shaped protrusions 130A, 130B, 130C of the resonance membranes vary from 3.2 mm. to 40 mm. The height of the plateau-shaped protrusion is best from one to two times the diameter of the sound communication opening 120 of base member 123, (ranging from 1.2 mm to 6.4 mm). A preferable body sound detection result will be obtained with the use of chestpieces having dimensions as stated hereinabove. Since the stethoscopic apparatus of the present invention does not have the O-ring or diaphragm fixation rim of the conventional stethoscope, the limitation associated with the free vibration of the resonance member as a result of the vibration of the viscera and body surface can be complete eliminated, and high resolution abilities in the detection of body sounds may be realized, especially in the relation to the heart and breathing sounds which are so important in the differential diagnosis of cardiac diseases and pulmonary diseases. In addition, due to the fact that a resonance chamber is compulsorily provided during the operation of the stethoscopic apparatus, a perfect diagnosis may be achieved.

Figure 8:
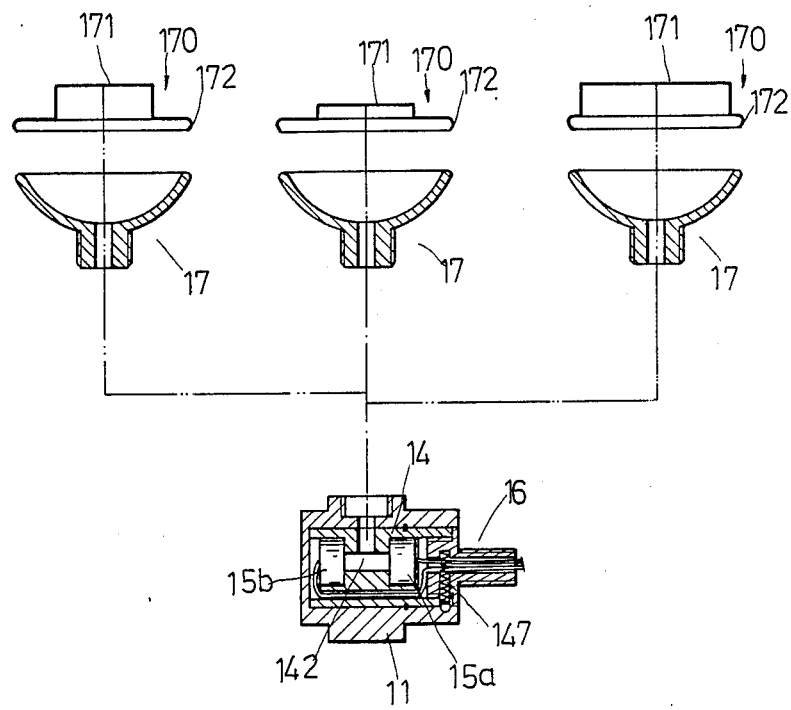
FIG. 8 is a schematic sectional view of the chestpieces in accordance with a second embodiment of the stethoscopic apparatus of the present invention.

Referring to FIG. 8 which shows schematic sectional views of the chestpiece assemblies according to a second embodiment of the present invention, the base member of each chestpiece 17 is bell-shaped, suitable for detecting the body sounds of lower frequencies. The configuration of the resonance membrane 170 having a plateau shaped protrusion 171 and an engaging rim 172 is the same as that of the chestpieces in FIG. 7. Again this assembly of Ford chestpieces boasts the improvement of a better body contact situation and a higher resolution ability for the direction of lower-pitch body sounds. Since a sealed resonance chamber will be established during the operation of the stethoscopic apparatus, improved diagnostic results can be obtained, especially if the auscultation site is covered with bandages.

Although the stethoscopic apparatus of the present invention has been described by way of preferred embodiments, it should be noted that changes and modifications are still possible for those skilled in the art without departing from the spirit of the present invention.

What is claimed is:

1. A stethoscopic apparatus comprising:
   a handle member both for the installation of sound transmission circuit devices and for use as a handle;
   a chestpiece assembly having a housing member with a rotatable shaft member positioned therein, a plurality of chestpieces attached on said housing member; and
   an adaptor means disposed between said handle member and said chestpiece assembly, having means for connecting with said handle member and said rotatable shaft member of said chestpiece assembly;
   wherein each of said chestpieces comprises a substantially concaved disc-shaped base member having a stem formed thereon and a sound transmission opening formed in the stem, and a resonance membrane having a shape conforming to that of said base member; said resonance membrane further including an engaging rim for engaging with said base member and a plateau-shaped protrusion integral with said membrane;
   said plateau-shaped protrusions having a height of about one to two times the diameter of said sound transmission opening of said base member of said chestpiece.

2. A stethoscopic apparatus as claimed in claim 1, wherein said plateau-shaped protrusion has a height of about 1.2 mm. to 6.4 mm.

3. A stethoscopic apparatus as claimed in claim 1, wherein said plateau-shaped protrusion has a diameter of about 3.2 mm. to 40.0 mm.

4. A stethoscopic apparatus as claimed in claim 1, wherein said base member is bell-shaped for a better detection of the body sounds of lower frequencies.

5. A stethoscopic apparatus as claimed in claim 1, wherein said chestpiece assembly further comprises clip means positioned between said housing member and said rotatable shaft for preventing relative axial movement therebetween.

6. A stethoscopic apparatus as claimed in claim 5, wherein said housing member and said rotatable shaft each include an annular recess formed therein for cooperatively receiving said clip means.

7. A chestpiece adopted in a stethoscopic apparatus comprising:
   a substantially concave disc-shaped base member having a stem formed thereon with a sound transmission opening formed in said stem; and
   a resonance membrane having a periphery conforming to that of said base member, and a plateau-shaped protrusion integral with said membrane and extending outwardly with respect to said base member to form a sealed resonance chamber between said base member and said resonance membrane;
   said resonance membrane being made of plastic polymers.

8. A chestpiece as claimed in claim 7, wherein said periphery of said resonance membrane is thermal set and forms an engaging rim for engaging with said base member of the chestpiece.

9. A chestpiece as claimed in claim 7, wherein said plateau-shaped protrusion has a diameter of about 3.2 mm. to 40.0 mm.

10. A chestpiece adopted in a stethoscopic apparatus, comprising:
    a substantially concave disc-shaped base member having a stem formed thereon with a sound transmission opening formed in said stem; and
    a resonance membrane having a periphery conforming to that of said base member, and a plateau-shaped protrusion integral with said membrane and extending outwardly with respect to said base member to form a sealed resonance chamber between said base member and said resonance membrane;
    said plateau-shaped protrusion having a height of one to two times the diameter of said sound transmission opening.

11. A chestpiece as claimed in claim 10, wherein said plateau-shaped protrusion has a height of about 1.2 mm. to 6.4 mm.

12. A stethoscopic apparatus comprising,
    a handle both for the installation of sound transmission circuit devices and for use as a handle;
    a chestpiece assembly having a housing member, including a rotatable shaft member rotatably mounted therein;
    a plurality of chestpieces removably mounted on said housing member; and
    adaptor means disposed between said handle member and said chestpiece assembly, said adaptor means including means for connecting said handle member to the rotatable shaft member of said chestpiece assembly, each of said chestpieces comprising a substantially concaved disc-shaped base member having a stem formed thereon and a sound transmission opening formed in the stem, and a resonance membrane having a shape conforming to that of its associated base member, said resonance membrane further including an engaging rim for engaging with said base member and a plateau-shaped protrusion integral with said membrane, the protrusions on each of said chestpieces having a different diameter than the protrusions on the other chestpieces.

* * * * *